United States Patent [19]
Sun et al.

[11] Patent Number: 6,051,758
[45] Date of Patent: *Apr. 18, 2000

[54] RECOMBINANT SWEET PROTEIN MABINLIN

[75] Inventors: Samuel S. M. Sun; Liwen Xiong, both of Honolulu, Hi.; Zhong Hu, Yunnan; Hang Chen, Beijing, both of China

[73] Assignee: University of Hawaii, Honolulu, Hi.

[*] Notice: This patent is subject to a terminal disclaimer.

[21] Appl. No.: 09/081,691

[22] Filed: May 20, 1998

Related U.S. Application Data

[62] Division of application No. 08/670,186, Jun. 21, 1996, Pat. No. 5,859,343
[60] Provisional application No. 60/000,480, Jun. 23, 1995.

[51] Int. Cl.[7] .............................. A01H 5/00; C12N 5/14; A23L 1/236
[52] U.S. Cl. .................... 800/295; 800/278; 435/69.1; 435/410; 435/419; 536/23.1; 536/23.6; 426/548
[58] Field of Search ................ 435/69.1, 320.1, 435/410, 419; 536/23.1, 23.6; 426/639; 800/295, 278

[56] References Cited

U.S. PATENT DOCUMENTS

| | | | |
|---|---|---|---|
| 4,771,000 | 9/1988 | Verrips et al. | 435/69.1 |
| 4,891,316 | 1/1990 | Verrips et al. | 435/69.1 |
| 4,966,842 | 10/1990 | Verrips et al. | 435/69.1 |
| 5,221,624 | 6/1993 | Blair et al. | 435/252.33 |
| 5,234,834 | 8/1993 | Fischer et al. | 435/320.1 |
| 5,346,998 | 9/1994 | Hellekant et al. | 536/23.6 |
| 5,741,537 | 4/1998 | Hellekant et al. | 426/548 |

FOREIGN PATENT DOCUMENTS

| | | |
|---|---|---|
| WO 85/01746 | 4/1985 | WIPO. |
| WO 87/03007 | 5/1987 | WIPO. |
| WO 88/10265 | 12/1988 | WIPO. |
| WO 90/07580 | 7/1990 | WIPO. |
| WO 92/01790 | 2/1992 | WIPO. |

OTHER PUBLICATIONS

Liu, X. et al., "Purification, complete amino acid sequence and structural characterization of the heat–stable sweet protein, mabinlin II," *Eur J Biochem* (1993) 211:281–287.
Nirasawa, S. et al., "Structures of heat–stable and unstable homologues of the sweet protein mabinlin," *Eur J Biochem* (1994) 223:989–995.
Edens, L. et al., "Cloning of cDNA encoding the sweet–tasting plant protein thaumatin and its expression in *Escherichia coli*," *Gene* (1982) 18:1–12.
Ausubel et al., "Current Protocols in Molecular Biology" vol. 1, 2.11.4–2.11.7, 8.2.8–8.2.13, 8.3.1.–8.5.9. (1994).
Nirasawa et al., *Gene* 181:225–227 (1996), and also cited as Biosis Abstract #99330012.
Nirasawa et al., *Eur. J. Biochem* 223: 989–995 (1994).
Sun et al., *Ann. N.Y. Acad. Sc.* 792:37–42 (1996).

*Primary Examiner*—John L. LeGuyader
*Attorney, Agent, or Firm*—Morrison & Foerster LLP

[57] ABSTRACT

Recombinant materials for the production of practical amounts of the sweet protein, mabinlin are provided. In addition, transgenic plants which have inherently sweetened edible parts result from modifying native plants containing edible parts to express the mabinlin gene. Single-chain forms of this protein which retain their sweetening property are also provided.

7 Claims, 3 Drawing Sheets

```
5'    AACACACACTCACCCAAAACCCTAGCAATGGCGAAGCTCATCTTCCTCTTC           51
                                  ↓-35
                                  M  A  K  L  I  F  L  F

GCGACCTTGGCTCTCTTCGTTCTCCTAGCGAACGCCTCCATCCAGACCACC          102
      A  T  L  A  L  F  V  L  L  A  N  A  S  I  Q  T  T
                                              1
                            -1  SS(A Chain)→
      GTTGTCGAGGTCGATGAAGAAGAAGACAACCAACTGTGGAGATGTCAGAGG          153
      V  V  E  V  D  E  E  E  D  N  Q  L  W  R  C  Q  R 10                            20
      CAGTTCCTGCAGCACCAGCGACTCCGGGCTTGCCAGCGGTTCATCCACCGA          204
      Q  F  L  Q  H  Q  R  L  R  A  C  Q  R  F  I  H  R 30      LINKER→              40
      CGAGCCCAGTTCGGCGGACAGCCCGATGAGCTTGAAGACGAAGTCGAGGAC          255
      R  A  Q  F  G  G  Q  P  D  E  L  E  D  E  V  E  D 50→
                         LS(B Chain)
      GACAACGATGACGAAAACCAGCCAAGGCGACCGGCGCTCAGACAATGCTGC          306
      D  N  D  D  E  N  Q  P  R  R  P  A  L  R  Q  C  C 60                          70
      AACCAACTGCGTCAAGTGGACAGACCTTGTGTTTGCCCTGTCCTCAGACAA          357
      N  Q  L  R  Q  V  D  R  P  C  V  C  P  V  L  R  Q 80                            90
      GCTGCCCAGCAGGTGCTCCAGCGACAAATAATCCAGGGTCCACAGCAGTTG          408
      A  A  Q  Q  V  L  Q  R  Q  I  I  Q  G  P  Q  Q  L 100
      AGGCGTCTCTTCGATGCCGCAAGAAATTTGCCCAACATCTGCAACATACCC          459
      R  R  L  F  D  A  A  R  N  L  P  N  I  C  N  I  P 110                              120
      AACATCGGAGCTTGCCCATTCAGAGCATGGCCCTAGGCCGAAACCATCCAG         510
      N  I  G  A  C  P  F  R  A  C  P  ***

TGGCTGACGGAGAGGATGTGTTTGTAGAATCGCATGTTGTAGTGTGTTAAT         561

AATGTTAGCATCGAGGCTAATGTACGAAACTAGCACTACTCCTAATAAGAG         612

GTTTCCAAGTTCTCTTAAAAAAAAAAAAAAAAAAAAAAAAAA    3'           629
```

FIG. 1

```
MBL  ↓
II   ATGGCGAAGCTCATCtTCCTCTTcgCgACCTTGGCtCTCTTcGTTCTCCTaGCgAACGCC
I    ATGGCGAAGCTCATCCTCCTCTTGACCACCTTGGCCCTCTTTGTTCTCCTGGCCAACGCC
III  ATGGCGAAGCTCATCCTCCTCTTGACCACCTTGGCCCTCTTTGTTCTCCTGGCCAACGCC

TCCATCcAgacCACCgttGTCGAGgTCGAtGAAGAAgaaGACAAC------------CAa
     TCCATCTACCGCACCACCGTCGAGCTCGACGAAGAA---GACAACGACGATGAGAACCAG
     TCCATCTACCGCACCACCGTCGAGCTCGACGAAGAA---GACAACGACGATGAGAACCAG CtgtgGagaTGtCagAGGCAGTTCCtGCAGCACCAGCgaCTCcGGGCTTGCCAGcGGTtC
     CCCCTG---TGCCGAAGGCAGTTCCAGCAGCACCAGCAcCTCAGGGCTTGCCAGAGGTAC
     CCCCTG---TGCCGAAGGCAGTTCCAGCAGCACCAGCAggTCAGGGCTTGCCAGAGGTAC ATCCaCCGaCGAGCCCAgttcGGcGGAcaGcCcGAtGAGCTTGAa------GACgaaGTC
     ATCCGCCGCCGAGCCCAAAGAGGTGGATTGGtAGACGAGCTaGAGCTAGAAGAC---GTC
     cTCCGCCGgCGAGCCCAAAGAGGTGGATTGGCAGACGAGCTTGAGCTAGAAGAC---GTC GAG---gacgacAACGAtGAcGAA------AACCAGCcaAGGcGACCGGCGCTCaGACaA
     GAGGAA------AACGAAGATGAAGACGAAAACCAGCAGAGGGGACCGGCGCTCCGACTA
     GAGGAA------AACGAAGATGAAGACGAAAACCAGCAGAGGGGACCGGCGCTCCGACTA TGCTGCAACCAACTGCGTCAaGTGgACAgACCtTGTGTTTGcCCtGTCCTCAGACAAGCT
     TGCTGCAACCAACTGCGTCAGGTGAACAAACCCTGTGTTTGTCCCGTCCTCAGACAAGCT
     TGCTGCAACCAACTGCGTCAGGTGAACAAACCCTGTGTTTGTCCCGTCCTCAGACAAGCT GCCCAgCAggtGCTccAgCgacaAatAATCcAgGGGTCCACagCAGtTGAGGCGTCTcTTC
     GCCCACCAACAGtTGTACCAGGGACAAATCGAAGGTCCACGCCAGGTGAGGCaaCTATTt
     GCCCACCAACAGCTGTACCAGGGACAAATCGAAGGTCCACGCCAGGTGAGGCGTCTATTC gatGCCGCaAGaAAtTTGCCCAACATCTGCAAcATaCCCaaCaTCGGAgctTGCCcaTTC
     AGAGCCGCCAGGAACTTGCCCAACATCTGCAAAATCCCCGCCGTCGGACGCTGCCAGTTC
     AGAGCCGCtAGGAACTTGCCCAACATCTGCAAAATCCCCGCCGTCGGACGCTGCCAGTTC

***
     AgagcATGGcccTAG
     ACGAGATGG---TAG
     ACGAGATGG---TAG
```

Sequence alignment of MBL I, II, and III showing:
- signal peptide
- Small subunit (A Chain)
- Linker
- Larger subunit (B Chain)

RECOMBINANT SWEET PROTEIN MABINLIN

The present application is a divisional of U.S. Ser. No. 08/670,186 filed Jun. 21, 1996, now U.S. Pat. No. 5,859,343, an allowed application, which is a continuation-in-part of U.S. provisional application Ser. No. 60/000,480, itself filed Jun. 23, 1995. The texts of both applications are incorporated by reference herein, as if set forth in their entirety.

TECHNICAL FIELD

The invention relates to a sweetener protein which can be added to food directly or which can be produced in situ in the edible parts of plants. More particularly, the invention concerns recombinant materials for production of the sweet protein mabinlin derived from the seeds of *Capparis masaikai*.

BACKGROUND ART

Demand is exceedingly great for sweetening agents which impart minimal caloric value to the foods in which they are contained. Low or noncaloric sweeteners are the key ingredient in low-calorie diets, and are particularly important for persons who are overweight, who are diabetics, or who are particularly susceptible to dental caries. Artificial sweeteners account for $1 billion of the $3.5 billion U.S. food additive market. Several well known compounds have been used, and continue to be used to some extent, as artificial sweeteners including saccharin, cyclamate, acesulfame K (ACK) and aspartame (which is a dipeptide). Aspartame, saccharin and ACK are approved for use in foods in the United States and other compounds such as sucralose and alitame are awaiting approval by the FDA.

In addition to these small molecules, two naturally occurring proteins have been suggested as low-calorie sweeteners, since they are many times sweeter than sugar. Thaumatins I and II are marketed under the brand name Talin® and are obtained from the fruits of the West African plant *Thaumatococcus daniellii*. Thaumatin is a nontoxic, noncarcinogenic protein that has a sweetness between 1600 and 3000 times that of sucrose on a weight basis. The other naturally occurring protein, monellin is derived from the "Serendipity Berry" and is 1500–3000 times sweeter than sugar. Both thaumatin and monellin denature at high temperatures, but monellin has been produced in a single-chain form and the single-chain form resists denaturation. See, for example, U.S. Pat. No. 5,234,834.

These two proteins and an additional protein, "brazzein" isolated from *Pentadiplandra brazzeana* Baillon have been manipulated recombinantly. See U.S. Pat. No. 5,346,998 (brazzein), PCT publications WO 85/01746 and WO 87/03007, and U.S. Pat. Nos. 4,771,000; 4,891,316; 4,966,842; and 5,221,624 (thaumatins) and EP 374157 B1 (single-chain monellin). Refolding of recombinant thaumatin has been described in European patent EP 255823 B, and single-chain monellin has been produced in transgenic plants to confer inherent sweetness (PCT application WO 92/01790). A yeast expression system for single-chain monellin has also been described in WO 90/07580.

The sweetener protein that forms the subject of the present invention, mabinlin (MBL), is derived from the seeds of *Capparis masaikai*. It is a heterodimer and exists in at least five isoforms. The complete amino acid sequence of one of these isoforms, mabinlin II (MBLII), was described by Liu, X. et al. *Eur J Biochem* (1993) 211:281–287. According to this article, the A chain of mabinlin II contains 33 amino acids; the B chain contains 72. The article shows that MBLII has considerable homology with a 2S seed storage protein 3(AT2S3) derived from *A. thaliana*. The dipeptide is water-soluble and is approximately 400 times sweeter than sucrose. Despite being a heterodimer, it exhibits high heat stability and is still sweet after 48 hours at 85° C.

The complete amino acid sequence of three other isoforms, I-1, III and IV were reported by Nirasawa et al., *Eur J Biochem* (1994) 223:989–995. As described by this article, there is a high degree of sequence identity among the amino acid sequences of these isoforms. MBLIII and IV, like MBLII, are heat stable while MBLI-1 is sensitive to high temperature treatment; i.e., loss of sweet activity after 1 hour incubation at 80° C.

The present invention provides recombinant materials for the production of mabinlin in practical amounts and for the production of transgenic plants containing inherently sweet edible parts by virtue of production of mabinlin in situ. Furthermore, production of single-chain mabinlin is provided.

DISCLOSURE OF THE INVENTION

The invention relates to recombinant materials useful in the production of the sweetener protein mabinlin (MBL) and to the modified foodstuffs resulting from incorporation of the recombinant form of this protein. The foodstuffs may be "natural" in that they are the edible parts of plants which have been modified to express the mabinlin-encoding gene. Availability of the gene encoding MBLII permits retrieval of genes encoding additional isoforms.

Thus, in one aspect, the invention is directed to a composition of DNA molecules which consists of DNA molecules comprising a nucleotide sequence encoding a mabinlin isoform protein or a subunit thereof. In another aspect, the invention is directed to expression systems comprising the coding sequence for a mabinlin protein or one of its subunits operably linked to control sequences capable of effecting its expression. The invention also relates to cells, including microorganisms and plant cells modified to contain these expression systems and to transgenic plants modified to contain them. In another aspect, the invention relates to a single-chain form of mabinlin.

In still other aspects, the invention relates to methods to sweeten food compositions by including in said compositions a sweetening amount of the recombinant mabinlin protein of the invention and to the resulting food compositions, and to methods to modulate MBL expression using antisense constructs.

BRIEF DESCRIPTION OF THE DRAWINGS

FIG. 1 (SEQ ID NO:1 and SEQ ID NO:2) shows the nucleotide and deduced amino acid sequence of mabinlin II cDNA. As shown, the cDNA encodes a prepromabinlin; the open reading frame encodes 155 amino acids; the first 35 of these (−35 to −1) represent a signal peptide presumably lost when the dipeptide is secreted. Amino acids numbered 1–33 in the figure represent the A chain; this is followed by a 14-amino acid prosequence which is evidently lost when the mature dimer is formed. Amino acids numbered 48–119 represent the B chain. The last amino acid of the prepromabinlin, i.e., residue 120, proline, is apparently cleaved off when the mature dimer is formed. In the Figure, ↓ (down arrow) indicates translation start; *, translation stop; underlining indicates putative polyadenylation signal; single letters (second line of text), amino acid sequences in the subunits of mature mabinlin protein; SS, small subunit; and LS, large subunit.

FIG. 2 shows the nucleotide sequences of cDNAs encoding the mabinlin isoforms MBLI (SEQ ID NO:3), MBLII (SEQ ID NO:1), and MBLIII (SEQ ID NO:5). Identical nucleotides are in capital letters, and dashed lines indicate deletions. Translation initiation is indicated by the arrow and the stop codon by three asterisks.

MODES OF CARRYING OUT THE INVENTION

The invention provides recombinant materials for the production of mabinlin protein. The use of mabinlin as a sweetener is limited by its native availability only in the seeds of the *Capparis masaikai* plant. These plants grow in the subtropical region of the Yunan Province of China, and the mature seed has been used as a traditional Chinese medicine. Those living in the region chew the seeds for their sweetness. However, the seeds themselves represent an impractical source for obtaining the sweetener protein which, if produced recombinantly, can be recovered and used to sweeten food compositions and feed stuffs.

In addition, plants containing edible parts can be modified to transgenic forms to express the genes encoding the mabinlin protein so as to result in enhanced sweetness of the fruits or vegetative portions of these plants.

The MBL protein, produced recombinantly in practical amounts, can be used to sweeten foods and beverages. Only small quantities are needed to supplement the flavoring of juices, carbonated beverages, and other soft drinks. The sweeteners can also be used as sugar substitutes in hot beverages such as coffee and tea since the MBL heterodimer is stable at elevated temperatures. MBL can also be used to sweeten animal feeds, and can be used in a variety of products such as chewing gum, toothpaste, mouthwash, dental hygiene products, and pharmaceuticals. In addition, MBL can be used in foodstuffs generally where sweetening may be desired such as meat products, instant soups, yogurt, desserts, cereals, and so forth.

Figure 1:
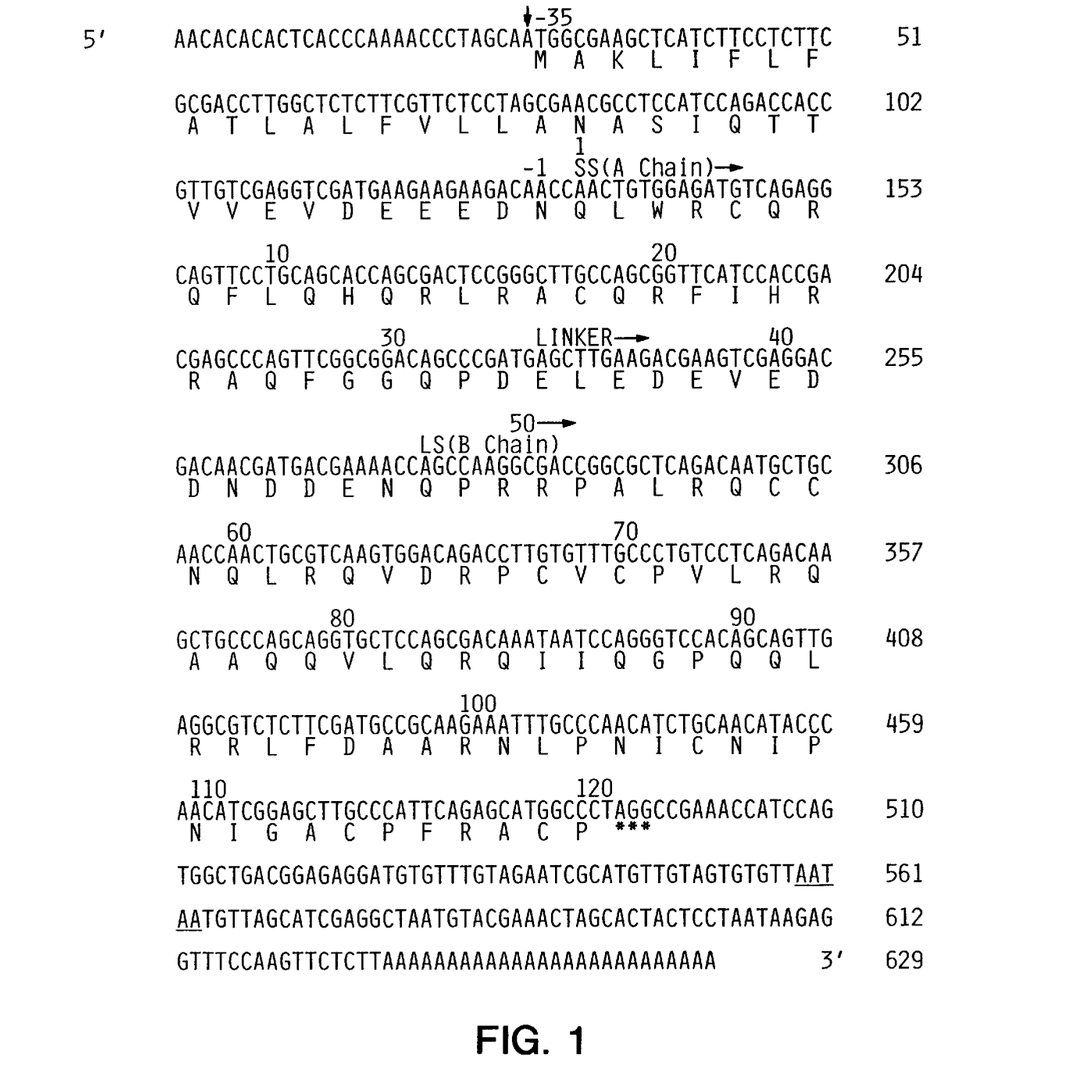
Figure 3:
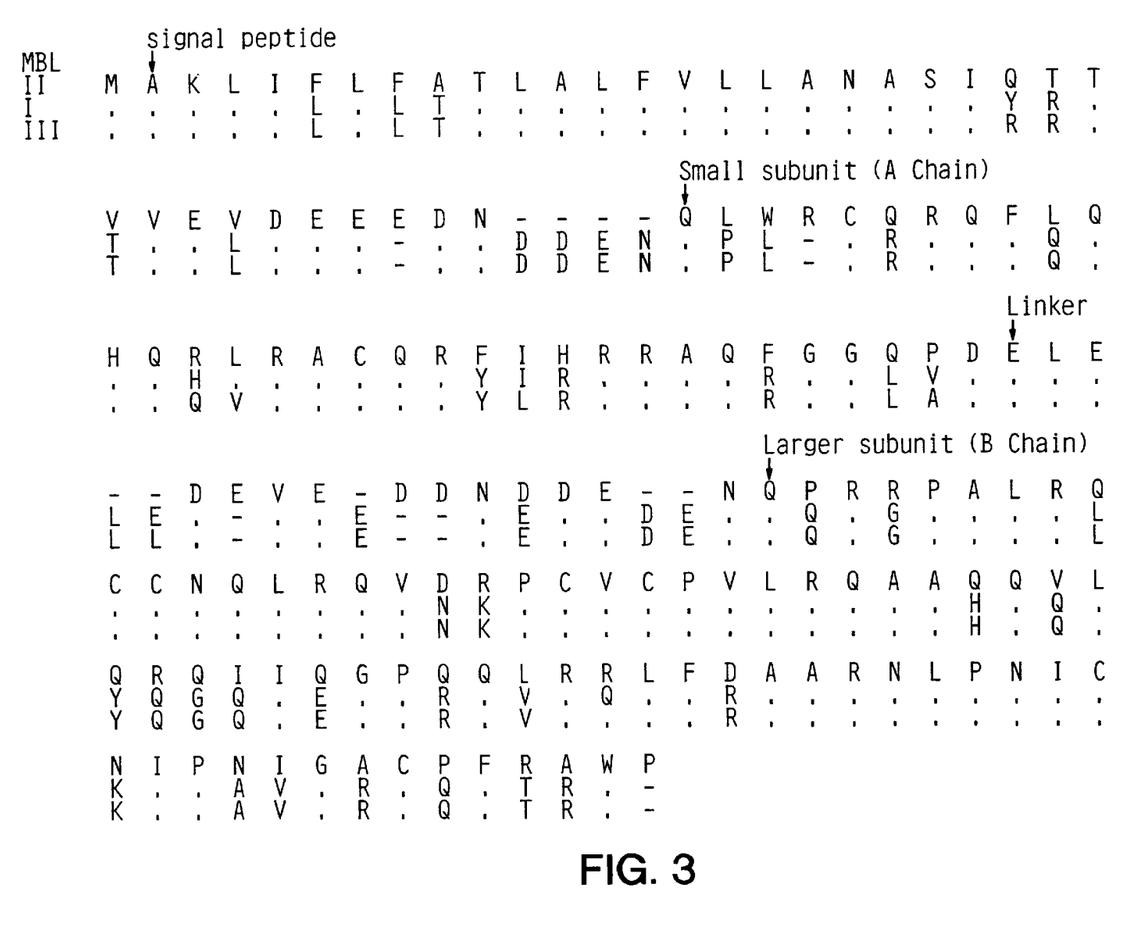
FIG. 3 (SEQ ID NO:2, SEQ ID NO:4, and SEQ ID NO:6) shows the deduced amino acid sequences of the preproproteins encoded by the nucleotide sequences of FIG. 2. The proteins are arranged to reflect their homology; dots indicate amino acid sequences in MBLI and MBLIII identical with those shown for MBLII, dashes indicate gaps resulting from maximum sequence alignment.

As used herein, "mabinlin protein" or "MBL protein" refers to a sweet protein containing amino acid sequences corresponding to those of the A and/or B subunits of the MBL protein shown in FIGS. 1–3 herein and their allelic variants. By "corresponds to" is meant that the amino acid sequences are those shown in the figures as describing the A and B subunits or the amino acid sequences of these subunits which are encoded by nucleotide sequences that hybridize under stringent conditions to the complements of the DNA sequences encoding the subunits there shown, e.g., to the complements of the nucleotide sequences set forth as MBLI, II or III in FIG. 2.

"Stringent conditions" refers to conditions that are generally understood in the art. For purposes of the present application, stringent conditions may be defined as washing in 0.1×SSC and 0.1% SDS at 68° C.

Provided the amino acid sequences corresponding to the A and/or B subunits are present, and the protein is sweet, the protein is defined as an MBL protein. Thus, the mabinlin protein may exist as the A or B subunit alone, as a dimer wherein the A and B subunits are both present, but not in a contiguous peptide sequence, optionally linked through disulfide or other covalent linkages, or the A and B amino acid sequences may exist on a single peptide/protein molecule, such as the proprotein precursor natively formed, or the prepro precursor natively formed, or the A and B subunits may be linked through a heterologous amino acid sequence. Thus, MBL or mabinlin protein is defined as any protein which retains sweet activity—i.e., when supplied at a reasonable concentration, such as 1 mg/ml, is detectably sweet by a taste test, and which contains the amino acid sequences corresponding to those of the A and/or B subunits shown in FIGS. 1–3.

In constructing the recombinant materials of the invention, the protein encoding sequences may be designed to generate a proprotein which contains a linker of 3–20 amino acids, preferably 12–18, and more preferably 14–16 amino acids, which is cleavable at least in some hosts to obtain the separate subunits. Alternatively, such constructs can be used in recombinant hosts lacking the proteases necessary for such cleavage. Provided the single-chain form of the "proprotein" remains sweet, the single-chain form itself is useful in the methods of the invention.

Production of MBL Protein

In addition to standard peptide synthesis methods, for production of the MBL protein as a commercial sweetener, typical recombinant production systems can be used. The expression systems comprising the A and B subunits can be constructed separately or on a single DNA molecule. The subunits can be produced as separate units or in the form of a proprotein analogous to the native proprotein, which is then processed to assemble the heterodimer. Alternatively, if produced in hosts, such as procaryotes, which do not process the precursor, the MBL protein can be produced in a single-chain "pro" form. This single-chain form is heat stable and retains sweetener activity. A single chain "pro" form can also be produced by designing or modifying the existing linker sequence that will not be cleavable by the target transgenic cells.

If secretion is desired, the preproprotein form may be used, or the A and B subunits may be separately supplied with signal peptides. A signal peptide which represents that normally associated with the mabinlin preproprotein may be used, or heterologous signal peptides appropriate to the recombinant host may be substituted. For example, for production in procaryotic hosts, it may be advantageous to utilize signal peptides operable in such hosts, such as the penicillinase signal peptide. Alternatively, the A and B subunits can be produced intracellularly either as separate units or as fusion proteins, including a proprotein form. If fusion proteins not processed by the host are utilized, it may be advantageous to engineer enzymatic cleavage sites into the fusions to permit cleavage to the mature forms.

The single-chain mabinlin or the two individual mabinlin subunits, in some constructs, are produced in intracellular insoluble forms. The cells are then lysed and the proteins are solubilized using denaturant(s) and reducing agent(s) as is understood in the art. The solubilized proteins are renatured by folding and dimer formation through disulfide bonding (Latta et al., *BioTechnol* (1987) 5:1305–1324) and assayed for sweet activity.

In general, eucaryotic hosts are preferred if the processed dimer is desired. These include yeast wherein expression systems can be constructed to effect secretion using, for example, the yeast α factor, or mammalian cell lines, most commonly CHO cells. In these contexts, as well, the choice of expression system is a matter of routine optimization; the subunits can be produced separately in the same or different cell culture and assembled by the host cell or by postrecovery manipulations conducted in vitro. Techniques for production of recombinant proteins in a variety of eucaryotic cells are by now well known.

In addition, techniques are available for the production of recombinant proteins in the milk of transgenic animals. This production method can be used as a substitute for cell culture or may be used to produce milk products which are endogenously sweetened.

Similarly, recombinantly manipulated plant cells or plants may be used either as recombinant production methods generally, or may be modified so as to result in fruits and vegetables having an enhanced sweet taste. In this embodiment, the protein may be produced from plant cells in culture or by intact plants.

In some instances, it may be desirable to provide the sweetening effects of mabinlin protein to cell cultures in situ. For example, expression systems containing the gene encoding MBL protein or subunits can be transfected into the culture organisms used in production of yogurt, wine, beer and the like and the MBL will be produced along with the production of the desired product.

When used as a sweetener product, MBL may be extended by addition of a liquid or powders wherein the MBL constitutes about 0.1–99% by weight of the composition. Suitable extenders include, for example, inert powders such as cellulose and may include additional helpful ingredients such as antioxidants, preservatives, protease inhibitors, and so forth.

Production in Plants

Rather than providing the MBL as an independent product, the coding sequences for MBL can be inserted into specialized expression control sequences which are compatible with higher plants used to obtain transgenic plants to result in naturally sweetened plant products. Expression systems operable in plants may be used to transform explants or plant protoplasts, and these then regenerated into intact plants which are then genetically capable of production of sweeter forms of fruit or vegetable products. If MBL is to be provided in the dimeric form, expression systems for both chains should be transformed into the plant. The system for each chain may be placed on a separate vector, or the two systems may be supplied on a single vector. Although the primary effect is that of sweetening, it is understood that the provision of this protein can affect the overall flavor and cause general improvement in taste. In these embodiments, control regions which are functional either constitutively or in specialized tissues in plants are employed. Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, tuber-specific promoter, seed-specific promoters, etc. can also be used. Plants transformed with this expression system offer production of naturally sweetened fruits, vegetables, and seeds.

A large number of suitable control systems are available. For example, the cauliflower mosaic virus (CAMV) 35S promoter has been shown to be highly active in many plant organs and during many stages of development when integrated into the genome of trans genic plants including tobacco and petunia, and has been shown to confer expression in protoplasts of both dicots and monocots.

The CaMV 35S promoter has been demonstrated to be active in a wide variety of monocot and dicot plants with edible parts, including blackberry, carrot, maize, and potato.

Organ-specific promoters are also well known. For example, the E8 promoter is only transcriptionally activated during tomato fruit ripening, and can be used to target gene expression in ripening tomato fruit (Deikman and Fischer, *EMBO J* (1988)7:3315; Giovannoni et al. *The Plant Cell* (1989) 1:53). The activity of the E8 promoter is not limited to tomato fruit, but is thought to be compatible with any system wherein ethylene activates biological processes.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans R Soc London* (1986) B314:343.

These mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al. *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

A somewhat more sophisticated procedure was described in *Molecular Biology of the Cell*, Second Edition (1989) pages 261–262, edited by Alberts et al., Garland Publishing Incorporated, New York. In this procedure, mRNAs enriched for organ-specific nucleic acid sequences were used to construct the cDNA library. This method was also applied to tomato by Lincoln et al. *Proc Natl Acad Sci* (1987) 84:2793, and resulted in the production of the E8 cDNA clone used to isolate the E8 promoter illustrated herein.

The gene that encodes the organ-specific mRNA is then isolated by constructing a library of genomic DNA sequences from the plant. The genome library is screened with the organ-specific cDNA clone, and the sequence is determined. The promoter is then isolated. These procedures are now considered to be routine and are described in detail in Sambrook et al, *Molecular Cloning: A Laboratory Manual*, Second Edition (1989) Cold Spring Harbor Laboratory Press, Cold Spring Harbor.

Either a constitutive promoter (such as the CaMV or Nos promoter illustrated above) or a desired organ-specific promoter (such as the E8 promoter from tomato or alternate specific promoter isolated using organ-specific cDNA as described above) is then ligated to the appropriate encoding DNA. As described above, for production in plants as well as in cell culture or transgenic animals, the A and B subunits may be produced independently and assembled in situ or may be produced as the proprotein or preproprotein and processed by the recombinant host. Since the preproprotein is successfully processed to form the dimer in plant tissue, for production of the dimer in plants, expression systems containing a nucleotide sequence encoding the preproprotein are preferred. The expression system may be further optimized by employing supplemental elements such as transcription terminators and/or enhancer elements.

Thus, for expression in plants, the recombinant expression cassette will contain, in addition to the MBL-encoding sequence(s), a plant promoter region, a transcription initiation site (if the MBL-encoding sequence to be transcribed lacks one), and a transcription termination sequence. Unique restriction enzyme sites at the 5' and 3' ends of the cassette are typically included to allow for easy insertion into a pre-existing vector.

Sequences controlling eucaryotic gene expression have been extensively studied. Promoter sequence elements include the TATA box consensus sequence (TATAAT), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G(or T)NG (Messing, J. et al., in *Genetic Engineering in Plants*, Kosage, Meredith and Hollaender, eds. (1983) pp. 221–227). Other sequences conferring tissue specificity, response to environmental signals, or maximum efficiency of transcription may also be found in the promoter region. Such sequences are often found within 400 bp of the transcription initiation site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

As stated above, any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids (Herrera-Estrella et al., *Nature* (1983) 303:209–213). Viral promoters include the 35S and 19S RNA promoters of cauliflower mosaic virus (O'Dell et al., *Nature* (1985) 313:810–812). Plant promoters include the ribulose-1,3-disphosphate carboxylase small subunit promoter and the phaseolin promoter. The promoter sequence from the E8 gene and other genes in which expression is induced by ethylene may also be used. The isolation and sequence of the E8 promoter is described in detail in Deikman and Fischer, *EMBO J* (1988) 7:3315–3320.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently processed, DNA sequences which direct polyadenylation of the RNA are also commonly added to the vector construct (Alber and Kawasaki, *Mol and Appl Genet*, (1982) 1:419–434). Polyadenylation is of importance for expression of the mabinlin-encoding RNA in plant cells. Polyadenylation sequences include, but are not limited to the Agrobacterium octopine synthase signal (Gielen et al., *EMBO J* (1984) 3:835–846) or the nopaline synthase signal (Depicker et al., *Mol and Appl Genet* (1982) 1:561–573).

The resulting expression system or cassette is ligated into or otherwise constructed to be included in a recombinant vector which is appropriate for higher plant transformation. The vector may also contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range procaryotic origin of replication is included. A selectable marker for bacteria should also be included to allow selection of bacterial cells bearing the desired construct. Suitable procaryotic selectable markers also include resistance to antibiotics such as kanamycin or tetracycline.

Other DNA sequences encoding additional finctions may also be present in the vector, as is known in the art. For instance, in the case of Agrobacterium transformations, T-DNA sequences will also be included for subsequent transfer to plant chromosomes.

In addition, vectors can also be constructed that contain in-frame ligations between the sequence encoding the sweetening protein and sequences encoding other molecules of interest resulting in fusion proteins, by techniques well known in the art.

When an appropriate vector is obtained, transgenic plants are prepared which contain the desired expression system. A number of techniques are available for transformation of plants or plant cells. All types of plants are appropriate subjects for "direct" transformation; in general, only dicots can be transformed using Agrobacterium-mediated infection.

In one form of direct transformation, the vector is microinjected directly into plant cells by use of micropipettes to mechanically transfer the recombinant DNA (Crossway, *Mol Gen Genetics* (1985) 202:179–185). In another form, the genetic material is transferred into the plant cell using polyethylene glycol (Krens, et aL, *Nature* (1982) 296:72–74), or high velocity ballistic penetration by small particles with the nucleic acid either within the matrix of small beads or particles, or on the surface, is used (Klein, et al., *Nature* (1987) 327:70–73). In still another method, protoplasts are fused with other entities which contain the DNA whose introduction is desired. These entities are minicells, cells, lysosomes or other fusible lipid-surfaced bodies (Fraley, et al., *Proc Natl Acad Sci USA* (1982) 79:1859–1863).

DNA may also be introduced into the plant cells by electroporation (Fromm et al., *Proc Natl Acad Sci USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303:179–189). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel, *Nature* (1981) 298:85–88), promoters (Lawton et al, *Plant Mol Biol* (1987) 2:315–324) and structural genes for antibiotic resistance as a selection factor (Fraley et al., *Proc Natl Acad Sci* (1983) 80:4803–4807).

There are two classes of recombinant Ti and Ri plasmid vector systems now in use. In one class, called "cointegrate," the shuttle vector containing the gene of interest is inserted by genetic recombination into a nononcogenic Ti plasmid that contains both the cis-acting and trans-acting elements required for plant transformation as, for example, in the pMLJ1 shuttle vector of DeBlock et al., *EMBO J* (1984) 3:1681–1689 and the non-oncogenic Ti plasmid pGV3850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the nononcogenic Ti plasmid as exemplified by the pBIN19 shuttle vector described by Bevan, *Nucleic Acids Research* (1984) 12:8711–8721 and the non-oncogenic Ti plasmid PAL4404 described by Hoekma, et al., *Nature* (1983) 303:179–180. Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Transformation of monocots using Agrobacterium is more difficult, but has been achieved (Hooykas-Van Slogteren et al., *Nature* (1984) 311:763–764). There is growing evidence now that monocots in general can be transformed successfully by Agrobacterium. Using novel experimental approaches cereal species such as rye (de la Pena et al., *Nature* (1987) 325:274–276), maize (Rhodes et al., *Science* (1988) 240:204–207), and rice (Shimamoto et al, *Nature* (1989) 338:274–276) may now be thus transformed.

Identification of transformed cells or plants is generally accomplished by including a selectable marker in the transforming vector, or by obtaining evidence of successful bacterial infection. Plant cells which have been transformed can also be regenerated using known techniques.

Plant regeneration from cultured protoplasts is described in Evans et al., Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. After the expression cassette is stably incorporated into regenerated transgenic plants, it can be transferred to other plants by sexual crossing. Any of a number of standard breeding techniques can be used, depending upon the species to be crossed.

The plants are grown and harvested using conventional procedures, and the desired edible portions recovered. In some instances, the edible portions are directly consumed as in the case of, for example, fruits such as tomato, peach, pear, etc. This may also be true of vegetative parts such as carrots, celery, and potato; or of edible seeds, such as peanuts, pecans, or sunflower seeds. If the edible portion is to be used in prepared foodstuffs, the recipe for preparation may conveniently be altered to reduce the sweetening component which would otherwise be added. For example, endogenously sweetened pumpkin used to make pumpkin pudding or pie filling, endogenously sweetened apples used in applesauce or apple pie, and endogenously sweetened rice used in making rice pudding would be employed in recipes of reduced sugar content. Depending on the lability to heat exhibited by the particular embodiment chosen, adjustments of amounts may need to be made in accordance with the cooking steps in the preparation procedure. Other modifications and adjustments of recipes employing these endogenously sweetened edible parts will be apparent and readily made by practitioners of the culinary art.

Thus, the expression cassette providing for constitutive or specialized organ production of MBL, contained in a suitable vector, is transformed into plant cells or explants, which are then regenerated into stably transformed transgenic plants with edible parts having endogenously enhanced sweetness. These plants are then cultivated conventionally to yield edible portions with increased sweetness.

In addition to the production of transgenic plants and in bulk production of the mabinlin protein for use as a sweetener, the recombinant materials encoding the mabinlin subunits, proprotein or preprotein or portions thereof can be used as hybridization probes and for the design of PCR-type primers to obtain the genes encoding additional isoforms of mabinlin. Indeed, the retrieved gene for mabinlin II has been thus employed to obtain the genes encoding the preproproteins representing mabinlin I and mabinlin III. The recovery of such isoforms will employ standard hybridization conditions suitable for the length of probe employed so as to minimize the number of false positives but nevertheless result in identification of DNA encoding these alternative forms. The stringency of the hybridization conditions will, of course, vary with the length of probe employed and the expected homology of the genes encoding these isoforms. Selection of conditions of standard stringency is well known to practitioners of the art; stringency depends on temperature and length of wash as well as the strength of the wash buffers employed. As used herein, "standard hybridization conditions" represents those recognized by practitioners to be appropriate for the circumstances herein described.

In addition to the nucleotide sequences described in FIG. 2 which encode the mabinlin preproprotein, nucleotide sequences contained in the genome, including any intervening sequences and upstream and downstream control regions, are readily available through standard recovery techniques in view of the disclosure of the encoding nucleotide sequences. Standard chromosome walking techniques can be applied such as those described by Sambrook, J. et al. *Molecular Cloning—A Laboratory Manual*, 2nd Ed. Cold Spring Harbor Press, New York (1989) and by Dracopoli, N. et al. eds. *Current Protocols in Human Genetics*, J. Wiley & Sons, New York (1994).

Alternate Uses of the DNA

Any of the encoding nucleotide sequences, the nucleotide sequences represented in the surrounding regions of the genome, or their complements may be used in the design of primers or probes for recovery of the genes associated with the mabinlin isoforms using PCR or other related amplification techniques. Nucleotide sequences of approximately 15 nucleotides, but as few as 11 and, if preferred, additional nucleotides can be used as primers.

Portions of the nucleotide sequence complementary to that encoding portions of the mabinlin preproprotein or complementary to those in control regions on the same strand as the coding sequences can also be used in control of mabinlin production using antisense techniques. Antisense control of expression in plants is by now well established.

Example 1 below describes the recovery of the gene encoding mabinlin II preproprotein. The complete nucleotide sequence of the coding region and the deduced amino acid sequence are shown in FIG. 1. The native sequence is particularly useful in the design of primers, construction of probes, and the like, but it is also particularly favored as a substrate for transcription and translation into the encoded protein. The native sequence is believed to have evolved so as to result in an intermediate messenger RNA which has appropriate secondary structure to permit ease of translation. Adjustment of this native sequence may be required when particular recombinant hosts or expression systems are employed. Such optimization is, however, generally of a minor nature and these modifications may be made without a great deal of experimentation. Theoretically, any one of the multitude of degenerate sequences encoding the preproprotein or its subunits may be synthesized de novo; however, using the native sequence encoding the preproprotein or a subunit enhances the probability of efficient expression, either using the native sequence per se or a modest modification thereof.

In general, then, the recovery of cDNA as described in this example need not be repeated; the desired nucleotide sequence can be synthesized using commercially available techniques.

The following examples are intended to illustrate the invention but not to limit its scope.

EXAMPLE 1

Recovery of cDNAs Encoding Mabinlin Isoforms cDNAs encoding mabinlin isoforms were recovered from *Capparis masaikai* as follows:

The developing seeds of *C. masaikai* were collected in September 1994, in the border regions between South China and Vietnam. Total RNA was extracted from the seeds using the method of Hall et al., *Proc Natl Acad Sci* (1978) 75: 3196–3200. Poly($A^+$) RNA was isolated using the PolyATract mRNA isolation kit (Promega) and a cDNA library was constructed using the Lambda Zap II cDNA cloning system (Stratagene).

Since the mabinlin isoforms I, II, III and IV represent 30% of the total seed protein, mabinlin mRNA levels are likely to represent a large proportion of the poly($A^+$) RNA. Furthermore, analysis of the poly($A^+$) RNA isolated from *C. masaikai* by formaldehyde/agarose gel electrophoresis revealed a predominant RNA species of approximately 700 nucleotides, which is sufficient to encode mabinlin. On the basis of these observations, it was expected that sequencing a limited number of random clones from the *C. masaikai* cDNA library would be sufficient to identify clones of the mabinlin isoforms.

Thus, insert cDNA was prepared from 50 phage plaques randomly selected from the primary library. The insert size was determined, and 21 of the clones with inserts ranging from 600 to 1000 bp were selected for sequencing. By comparison with the known amino acid sequence of mabinlin II, it was determined that four cDNA clones encoded the mabinlin II sequence, two clones encoded the mabinlin I sequence, while the mabinlin III or IV sequence was represented by one clone. Mabinlin IV differs from mabinlin III in that its small subunit (A chain) is four amino acids shorter at its C-terminus. It is possible that mabinlin IV is derived from mabinlin III by post-translational processing, and thus both proteins would be translated from the same mRNA species.

EXAMPLE 2

Expression of Mabinlin II in Potato

Two mabinlin II (MBLII) chimeric genes have been subcloned into the Agrobacterium binary transfection vector, pBI121 (Jefferson et al., *EMBO J* (1987) 6:3901–3907). In the first construct, $Patatin_{Pro}$/MBLII/$NOS_{Ter}$, the full-length MBLII cDNA encoding the 5' and 3' untranslated regions, the signal peptide and linker sequence was inserted downstream of the tuber-specific patatin promoter, $Patatin_{Pro}$, (Wenzler et al., *Plant Mol Biol* (1989) 12: 41–50) and followed by the termination sequence from the nopaline synthase gene ($NOS_{ter}$) of the Agrobacterium Ti plasmid (Bevan et al., *Nucl Acid Res* (1983) 11:369–386; Bevan et al., *Nature* (1983) 304:184–187). In the second construct, CaMV $35S_{Pro}$/MBLII/$NOS_{Ter}$, the full-length MBLII cDNA was inserted downstream of the constitutive cauliflower mosaic virus 35S promoter (CaMV 35S) and again followed by $NOS_{ter}$. This second construct is useful for identifying transfectants and analyzing the expression and processing of mabinlin in early callus and small plantlet stages. The $Patatin_{Pro}$/MBLII/$NOS_{Ter}$ and the CaMV $35S_{Pro}$/MBLII/$NOS_{Ter}$ plasmids were transfected into potato (*Solanum tuberosum* L. cv. Russet Burbank) using the potato microtuber disc transfection method of Ishida et al., *Plant Cell Reporter* (1989) 8:325–328). Intact plants were regenerated from the transformants, and the transgenic plants were identified by marker genes contained in the constructs. Intact plants harboring the MBLII gene were identified and confirmed by Southern blot using the MBL nucleotide sequence shown in FIG. 1 or its complement as a probe. Transcription of the MBLII gene was confirmed by Northern analysis. The transgenic plants express high levels of active mabinlin II protein; the protein is detected by Immunodot blot analysis using antibodies immunospecific for MBLII.

To further enhance the expression level of mabinlin, transfection vectors containing 2, 3, and 4 copies of the chimeric $Patatin_{Pro}$/MBLII/$NOS_{Ter}$ gene are constructed for multi-copy integration. Patatin is encoded by a large multigene family, having some 50–70 members in a tetraploid genome (Twell and Ooms, *Mol Gen Genet* (1988) 212:325–336). Integration of several copies of the MBLII gene enhances the expression level. Although co-suppression has been shown to occur as a result of adding extra copies of a homologous gene in a transgenic plant (van der Krol et al., *The Plant Cell* (1990) 2:291–299), this suppression should not occur with storage protein genes which typically exist as a multigene family.

EXAMPLE 3

Expression of Mabinlin II in Cultured Plant Cells

Large-scale suspension plant cell culture has been demonstrated for the production of shikonin, ginseng and berberine (Misawa, in *Plant Cell Culture in Japan* (1991) Komaine et al. eds, pp.3–7) and offers an attractive alternative to both whole plant extraction and microbial systems for the production of recombinant products. In general, recombinant plant proteins expressed in vitro in suspension plant cell culture are properly processed and modified. *Anchusa officinalis* has been chosen as a host plant cell (Su et al., *Biotechnol Bioeng* (1993) 42:884–890) and has the following attributes: 1) a high growth rate and a moderate specific oxygen demand, 2) a very high cell density can be achieved via culture perfusion, 3) the suspension culture is homogeneous with very few large cell aggregates and 4) a relatively low cell culture viscosity.

An expression vector containing an *A. officinalis* promoter from a gene expressed at high levels is constructed as follows. An abundantly expressed *A. officinalis* protein is identified, and the portion of the gene encoding the promoter is isolated using standard cloning procedures. The full-length mabinlin II cDNA of Example 1 is subcloned downstream from the promoter in a replicable plasmid and the chimeric *A. officinalis* promoter/MBLII expression plasmid is transfected into *A. officinalis* by particle bombardment technology (Klein et al., *Nature* (1987) 327:70–73). The bioreactor developed by Su (*External loop perfusion air-lift bioreactor* (1994) U.S. Pat. No. 5,342,781) is used for mass suspension culture of the transfected cells. The production and processing of the mabinlin protein by these cells is then assayed.

EXAMPLE 4

Expression of Mabinlin II in Microorganisms

A. Using polymerase chain amplification technology (Saiki et al., *Science* (1988) 239:487–491) a sequence encoding the small subunit A, the 14 amino acid linker and the large subunit B of mabinlin II is generated, thus deleting the sequences encoding the signal peptide and the adjacent proline. The engineered coding sequence was inserted into the pLEX expression vector (Invitrogen) under the regulation of the $P_L$ promoter. This strong $P_L$ promoter is regulated by the lambda cI repressor which is expressed from the bacterial chromosome of the *E. coli* strain G1724 under the control of the tightly regulated trp promoter (La Vallie et al., *BioTechnol*(1993) 11:193–197). Expression of mabinlin in this system is induced by the addition of tryptophan to the media, and production of mabinlin is assessed by SDS-polyacrylamide gel electrophoresis. Mabinlin protein is purified by molecular sieve chromatography or sucrose gradient centrifugation, sweet activity of mabinlin is located among the resulting fractions by taste-testing.

*E. coli* lacks the specific protease(s) to cleave the mabinlin precursor. The 14 amino acid linker peptide between the small and large subunits is not excised, thus resulting in a single-chain mabinlin which retains the sweet activity of the dimer.

B. In a manner similar to that set forth in paragraph A, the genes encoding the mature small mabinlin subunit polypeptide and the mature large subunit are inserted into separate expression vectors and co-transformed into the bacterium for simultaneous expression in the cell. The expression products are then purified and assayed for sweet activity as in paragraph A.

C. Active mabinlin is produced in E. coli or yeast through the co-expression of mabinlin and PDI in the recombinant system, as described by Schultz et al., (*Ann NY Acad Sci* (1994) 721:148–157). In this system, overexpression of protein disulfide isomerase (PDI) (Creighton et al., *TIBTECH* (1995) 13:18–23) simultaneously with recombinant protein results in increased levels of secretion of multiple disulfide-bonded heterologous proteins.

EXAMPLE 5

Production of Single-Chain Mabinlin

Site-directed mutagenesis is used to alter the cleavage sites for the deletion of the "pro" sequence in order to effect production of the mabinlin protein as a single chain. The codon for the aspartic acid residue at position 34 at the C-terminus of the A subunit is mutated so as to encode a tyrosine residue in mutant A1 or to encode an alanine residue in mutant A2 as diagrammed below.

```
                                   Cleavage Site
Wild type:       Subunit A        ↓     Linker
                  G   G   Q   P   D   E   L   E   D
     5' -- GGC GGA CAG CCC GAT GAG CTT GAA GAC --- 3'  (positions 217–243 of SEQ ID NO:1)

Mutant A1:                        ↓
     5' -- GGC GGA CAG CCC TAT GAG CTT GAA GAC --- 3"  (SEQ ID NO:7)
                              Y Mutant A2:                        ↓
     5' -- GGC GGA CAG CCC GCT GAG CTT GAA GAC --- 3'  (SEQ ID NO:8)
                              A
```

Similarly, mutants L1 and L2 were generated by changing the codon for the asparagine residue immediately preceding the B subunit at position 47 in FIG. 1 to encode threonine in mutant L1 and isoleucine in mutant L2 as shown below:

Suitable expression vectors comprising an expression system for the resulting mutants represented by the combination of A1 and L1, A1 and L2, A2 and L1, and A2 and L$_2$ are then constructed and the corresponding proteins produced. In one embodiment, the expression system is compatible with plant cell production of the protein and uses the promoter and terminator sequences of the phaseolin gene (Slightom et al., *Proc Natl Acad Sci USA* (1983) 80:1897–1901). The resulting expression systems are then transferred into tobacco using the methods set forth herein, in Example 2, using Agrobacterium-mediated transfer. The leaf disk transformation procedure of Horsch et al. *Science* (1985) 227:1229–1231 is used, and transgenic tobacco plants are regenerated. The production and processing of the resulting wild-type and mutant mabinlin proteins in the developing transgenic tobacco seeds are then analyzed.

---

We claim:

1. An edible plant part or food composition that comprises mabinlin protein, which protein is produced by a method which comprises the steps of:
   (a) culturing a microorganism, cell line, plant cell, plant part or plant modified to contain a DNA molecule that comprises a first nucleotide sequence that encodes the amino acid sequence of a mabinlin protein subunit A, and a second nucleotide sequence that encodes the amino acid sequence of a mabinlin protein subunit B, from which can be expressed a mabinlin protein having sweet activity, under conditions wherein said expression system is operable to produce said mabinlin protein, and
   (b) recovering said mabinlin protein from said culture, or recovering an edible portion of said plant.

2. A method to sweeten a food composition, which method comprises adding to said composition an effective amount of mabinlin protein, which protein is produced by the method of:
   (a) culturing a microorganism, cell line, plant cell, plant part or plant modified to contain a DNA molecule that comprises a first nucleotide sequence that encodes the amino acid sequence of a mabinlin protein subunit A, and a second nucleotide sequence that encodes the amino acid sequence of a mabinlin protein subunit B, from which can be expressed a mabinlin protein having sweet activity, under conditions wherein said expression system is operable to produce said mabinlin protein, and
   (b) recovering said mabinlin protein from said culture.

3. An edible composition that comprises mabinlin protein, which protein is produced by the method of:
   (a) culturing a microorganism, cell line, plant cell, plant part or plant modified to contain a DNA molecule that comprises a first nucleotide sequence that encodes the amino acid sequence of a mabinlin protein subunit A, and a second nucleotide sequence that encodes the amino acid sequence of a mabinlin protein subunit B, from which can be expressed a mabinlin protein having sweet activity, under conditions wherein said expression system is operable to produce said mabinlin protein, and
   (b) recovering said mabinlin protein from said culture.

4. A method of making a composition using mabinlin protein comprising:
   (a) culturing a microorganism, cell line, plant cell, plant part or plant modified to contain a DNA molecule that comprises a first nucleotide sequence that encodes the amino acid sequence of a mabinlin protein subunit A, and a second nucleotide sequence that encodes the amino acid sequence of a mabinlin protein subunit B, from which can be expressed a mabinlin protein having sweet activity, under conditions wherein said expression system is operable to produce said mabinlin protein, and
   (b) recovering said mabinlin protein from said culture, said method comprising the step of adding said protein to the composition in order to sweeten it.

5. A method of expressing a gene encoding mabinlin protein in a a microorganism, cell line, plant cell, plant part or plant which method comprises treating said microorganism, cell line, plant cell, plant part or plant with a composition of DNA molecules that consists of DNA molecules comprising a nucleotide sequence complementary to that of:
   (a) the cDNA for mabinlin isoform MBL-I (SEQ ID NO:3);
   (b) the cDNA for mabinlin isoform MBL-II (SEQ ID NO:1);
   (c) the cDNA for mabinlin isoform MBL-III (SEQ ID NO:5); or (d) the cDNA for mabinlin isoform MBL-IV (MBL-IV subset of SEQ ID NO:5);

that is sufficient for expression.

6. An edible plant part or food composition that comprises single chain mabinlin protein free of components that accompany it in *Capparis masaikai*.

7. An edible plant part or food composition according to claim 6, wherein said single chain mabinlin protein contains mabinlin subunit A amino acid primary sequence and mabinlin subunit B amino acid primary sequence linked by a linker peptide of 3 to 20 amino acids.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 629 base pairs
      (B) TYPE: nucleic acid
      (C) STRANDEDNESS: double
      (D) TOPOLOGY: linear    (ii) MOLECULE TYPE: DNA (genomic)

(ix) FEATURE:
      (A) NAME/KEY: polyA_site
      (B) LOCATION: 629

(ix) FEATURE:
      (A) NAME/KEY: CDS
      (B) LOCATION: 28..492

(ix) FEATURE:
      (A) NAME/KEY: mutation
      (B) LOCATION: replace(229, "t")
      (D) OTHER INFORMATION: /gene= "mutant A1"
          /note= "codon changes from aspartic acid to tyrosine in mutant A1"

(ix) FEATURE:
      (A) NAME/KEY: mutation
      (B) LOCATION: replace(230, "c")
      (D) OTHER INFORMATION: /gene= "mutant A2"
          /note= "codon changes from aspartic acid to alanine for mutant A2"

(ix) FEATURE:
      (A) NAME/KEY: mutation
      (B) LOCATION: replace(272, "c")
      (D) OTHER INFORMATION: /gene= "mutant L1"
          /note= "codon changes from asparagine to threonine for mutant L1"

(ix) FEATURE:
      (A) NAME/KEY: mutation
      (B) LOCATION: replace(272, "t")
      (D) OTHER INFORMATION: /gene= "mutant L2"

/note= "codon changes from asparagine to isoleucine
for mutant L2"

(xi) SEQUENCE DESCRIPTION: SEQ ID NO:1:

```
AACACACACT CACCCAAAAC CCTAGCA ATG GCG AAG CTC ATC TTC CTC TTC           51
                             Met Ala Lys Leu Ile Phe Leu Phe
                              1               5

GCG ACC TTG GCT CTC TTC GTT CTC CTA GCG AAC GCC TCC ATC CAG ACC         99
Ala Thr Leu Ala Leu Phe Val Leu Leu Ala Asn Ala Ser Ile Gln Thr
         10                  15                  20

ACC GTT GTC GAG GTC GAT GAA GAA GAA GAC AAC CAA CTG TGG AGA TGT        147
Thr Val Val Glu Val Asp Glu Glu Glu Asp Asn Gln Leu Trp Arg Cys
 25                  30                  35                  40

CAG AGG CAG TTC CTG CAG CAC CAG CGA CTC CGG GCT TGC CAG CGG TTC        195
Gln Arg Gln Phe Leu Gln His Gln Arg Leu Arg Ala Cys Gln Arg Phe
                 45                  50                  55

ATC CAC CGA CGA GCC CAG TTC GGC GGA CAG CCC GAT GAG CTT GAA GAC        243
Ile His Arg Arg Ala Gln Phe Gly Gly Gln Pro Asp Glu Leu Glu Asp
             60                  65                  70

GAA GTC GAG GAC GAC AAC GAT GAC GAA AAC CAG CCA AGG CGA CCG GCG        291
Glu Val Glu Asp Asp Asn Asp Asp Glu Asn Gln Pro Arg Arg Pro Ala
                 75                  80                  85

CTC AGA CAA TGC TGC AAC CAA CTG CGT CAA GTG GAC AGA CCT TGT GTT        339
Leu Arg Gln Cys Cys Asn Gln Leu Arg Gln Val Asp Arg Pro Cys Val
             90                  95                 100

TGC CCT GTC CTC AGA CAA GCT GCC CAG CAG GTG CTC CAG CGA CAA ATA        387
Cys Pro Val Leu Arg Gln Ala Ala Gln Gln Val Leu Gln Arg Gln Ile
105                 110                 115                 120

ATC CAG GGT CCA CAG CAG TTG AGG CGT CTC TTT GAT GCC GCA AGA AAT        435
Ile Gln Gly Pro Gln Gln Leu Arg Arg Leu Phe Asp Ala Ala Arg Asn
                125                 130                 135

TTG CCC AAC ATC TGC AAC ATA CCC AAC ATC GGA GCT TGC CCA TTC AGA        483
Leu Pro Asn Ile Cys Asn Ile Pro Asn Ile Gly Ala Cys Pro Phe Arg
            140                 145                 150

GCA TGG CCC TAGGCCGAAA CCATCCAGTG GCTGACGGAG AGGATGTGTT                532
Ala Trp Pro
        155

TGTAGAATCG CATGTTGTAG TGTGTTAATA ATGTTAGCAT CGAGGCTAAT GTACGAAACT      592

AGCACTACTC CTAATAAGAG GTTTCCAAGT TCTCTTA                               629
```

(2) INFORMATION FOR SEQ ID NO:2:

(i) SEQUENCE CHARACTERISTICS:
        (A) LENGTH: 155 amino acids
        (B) TYPE: amino acid
        (D) TOPOLOGY: linear     (ii) MOLECULE TYPE: protein     (xi) SEQUENCE DESCRIPTION: SEQ ID NO:2:

```
Met Ala Lys Leu Ile Phe Leu Phe Ala Thr Leu Ala Leu Phe Val Leu
 1               5                  10                  15

Leu Ala Asn Ala Ser Ile Gln Thr Thr Val Val Glu Val Asp Glu Glu
             20                  25                  30

Glu Asp Asn Gln Leu Trp Arg Cys Gln Arg Gln Phe Leu Gln His Gln
         35                  40                  45

Arg Leu Arg Ala Cys Gln Arg Phe Ile His Arg Arg Ala Gln Phe Gly
     50                  55                  60

Gly Gln Pro Asp Glu Leu Glu Asp Glu Val Glu Asp Asp Asn Asp Asp
 65                  70                  75                  80
```

-continued

```
Glu Asn Gln Pro Arg Arg Pro Ala Leu Arg Gln Cys Cys Asn Gln Leu
             85                  90                  95

Arg Gln Val Asp Arg Pro Cys Val Cys Pro Val Leu Arg Gln Ala Ala
            100                 105                 110

Gln Gln Val Leu Gln Arg Gln Ile Ile Gln Gly Pro Gln Gln Leu Arg
            115                 120                 125

Arg Leu Phe Asp Ala Ala Arg Asn Leu Pro Asn Ile Cys Asn Ile Pro
130                 135                 140

Asn Ile Gly Ala Cys Pro Phe Arg Ala Trp Pro
145                 150                 155

(2) INFORMATION FOR SEQ ID NO:3:

(i) SEQUENCE CHARACTERISTICS:
        (A) LENGTH: 477 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..474

(xi) SEQUENCE DESCRIPTION: SEQ ID NO:3:

ATG GCG AAG CTC ATC CTC CTC TTG ACC ACC TTG GCC CTC TTT GTT CTC    48
Met Ala Lys Leu Ile Leu Leu Leu Thr Thr Leu Ala Leu Phe Val Leu
            160                 165                 170

CTG GCC AAC GCC TCC ATC TAC CGC ACC ACC GTC GAG CTC GAC GAA GAA    96
Leu Ala Asn Ala Ser Ile Tyr Arg Thr Thr Val Glu Leu Asp Glu Glu
            175                 180                 185

GAC AAC GAC GAT GAG AAC CAG CCC CTG TGC CGA AGG CAG TTC CAG CAG   144
Asp Asn Asp Asp Glu Asn Gln Pro Leu Cys Arg Arg Gln Phe Gln Gln
        190                 195                 200

CAC CAG CAC CTC AGG GCT TGC CAG AGG TAC ATC CGC CGC CGA GCC CAA   192
His Gln His Leu Arg Ala Cys Gln Arg Tyr Ile Arg Arg Arg Ala Gln
    205                 210                 215

AGA GGT GGA TTG GTA GAC GAG CTA GAG CTA GAA GAC GTC GAG GAA AAC   240
Arg Gly Gly Leu Val Asp Glu Leu Glu Leu Glu Asp Val Glu Glu Asn
220                 225                 230                 235

GAA GAT GAA GAC GAA AAC CAG CAG AGG GGA CCG GCG CTC CGA CTA TGC   288
Glu Asp Glu Asp Glu Asn Gln Gln Arg Gly Pro Ala Leu Arg Leu Cys
                240                 245                 250

TGC AAC CAA CTG CGT CAG GTG AAC AAA CCC TGT GTT TGT CCC GTC CTC   336
Cys Asn Gln Leu Arg Gln Val Asn Lys Pro Cys Val Cys Pro Val Leu
            255                 260                 265

AGA CAA GCT GCC CAC CAA CAG TTG TAC CAG GGA CAA ATC GAA GGT CCA   384
Arg Gln Ala Ala His Gln Gln Leu Tyr Gln Gly Gln Ile Glu Gly Pro
            270                 275                 280

CGC CAG GTG AGG CAA CTA TTT AGA GCC GCC AGG AAC TTG CCC AAC ATC   432
Arg Gln Val Arg Gln Leu Phe Arg Ala Ala Arg Asn Leu Pro Asn Ile
            285                 290                 295

TGC AAA ATC CCC GCC GTC GGA CGC TGC CAG TTC ACG AGA TGG            474
Cys Lys Ile Pro Ala Val Gly Arg Cys Gln Phe Thr Arg Trp
300                 305                 310

TAG                                                                477

(2) INFORMATION FOR SEQ ID NO:4:

(i) SEQUENCE CHARACTERISTICS:
```

(A) LENGTH: 158 amino acids
                (B) TYPE: amino acid
                (D) TOPOLOGY: linear (ii) MOLECULE TYPE: protein (xi) SEQUENCE DESCRIPTION: SEQ ID NO:4:

Met Ala Lys Leu Ile Leu Leu Leu Thr Thr Leu Ala Leu Phe Val Leu
 1               5                  10                  15

Leu Ala Asn Ala Ser Ile Tyr Arg Thr Thr Val Glu Leu Asp Glu Glu
             20                  25                  30

Asp Asn Asp Asp Glu Asn Gln Pro Leu Cys Arg Arg Gln Phe Gln Gln
         35                  40                  45

His Gln His Leu Arg Ala Cys Gln Arg Tyr Ile Arg Arg Arg Ala Gln
 50                  55                  60

Arg Gly Gly Leu Val Asp Glu Leu Glu Leu Glu Asp Val Glu Glu Asn
 65                  70                  75                  80

Glu Asp Glu Asp Glu Asn Gln Gln Arg Gly Pro Ala Leu Arg Leu Cys
             85                  90                  95

Cys Asn Gln Leu Arg Gln Val Asn Lys Pro Cys Val Cys Pro Val Leu
                100                 105                 110

Arg Gln Ala Ala His Gln Leu Tyr Gln Gly Gln Ile Glu Gly Pro
            115                 120                 125

Arg Gln Val Arg Gln Leu Phe Arg Ala Ala Arg Asn Leu Pro Asn Ile
        130                 135                 140

Cys Lys Ile Pro Ala Val Gly Arg Cys Gln Phe Thr Arg Trp
145                 150                 155

(2) INFORMATION FOR SEQ ID NO:5:

(i) SEQUENCE CHARACTERISTICS:
                (A) LENGTH: 477 base pairs
                (B) TYPE: nucleic acid
                (C) STRANDEDNESS: double
                (D) TOPOLOGY: linear (ii) MOLECULE TYPE: DNA (genomic)

(ix) FEATURE:
                (A) NAME/KEY: CDS
                (B) LOCATION: 1..474

(xi) SEQUENCE DESCRIPTION: SEQ ID NO:5:

ATG GCG AAG CTC ATC CTC CTC TTG ACC ACC TTG GCC CTC TTT GTT CTC        48
Met Ala Lys Leu Ile Leu Leu Leu Thr Thr Leu Ala Leu Phe Val Leu
160                 165                 170

CTG GCC AAC GCC TCC ATC TAC CGC ACC ACC GTC GAG CTC GAC GAA GAA        96
Leu Ala Asn Ala Ser Ile Tyr Arg Thr Thr Val Glu Leu Asp Glu Glu
175                 180                 185                 190

GAC AAC GAC GAT GAG AAC CAG CCC CTG TGC CGA AGG CAG TTC CAG CAG       144
Asp Asn Asp Asp Glu Asn Gln Pro Leu Cys Arg Arg Gln Phe Gln Gln
                195                 200                 205

CAC CAG CAG GTC AGG GCT TGC CAG AGG TAC CTC CGC CGG CGA GCC CAA       192
His Gln Gln Val Arg Ala Cys Gln Arg Tyr Leu Arg Arg Arg Ala Gln
            210                 215                 220

AGA GGT GGA TTG GCA GAC GAG CTT GAG CTA GAA GAC GTC GAG GAA AAC       240
Arg Gly Gly Leu Ala Asp Glu Leu Glu Leu Glu Asp Val Glu Glu Asn
        225                 230                 235

GAA GAT GAA GAC GAA AAC CAG CAG AGG GGA CCG GCG CTC CGA CTA TGC       288
Glu Asp Glu Asp Glu Asn Gln Gln Arg Gly Pro Ala Leu Arg Leu Cys
240                 245                 250

```
TGC AAC CAA CTG CGT CAG GTG AAC AAA CCC TGT GTT TGT CCC GTC CTC      336
Cys Asn Gln Leu Arg Gln Val Asn Lys Pro Cys Val Cys Pro Val Leu
255                 260                 265                 270

AGA CAA GCT GCC CAC CAA CAG CTG TAC CAG GGA CAA ATC GAA GGT CCA      384
Arg Gln Ala Ala His Gln Gln Leu Tyr Gln Gly Gln Ile Glu Gly Pro
                275                 280                 285

CGC CAG GTG AGG CGT CTA TTC AGA GCC GCT AGG AAC TTG CCC AAC ATC      432
Arg Gln Val Arg Arg Leu Phe Arg Ala Ala Arg Asn Leu Pro Asn Ile
            290                 295                 300

TGC AAA ATC CCC GCC GTC GGA CGC TGC CAG TTC ACG AGA TGG              474
Cys Lys Ile Pro Ala Val Gly Arg Cys Gln Phe Thr Arg Trp
        305                 310                 315

TAG                                                                  477
```

(2) INFORMATION FOR SEQ ID NO:6:

(i) SEQUENCE CHARACTERISTICS:
        (A) LENGTH: 158 amino acids
        (B) TYPE: amino acid
        (D) TOPOLOGY: linear     (ii) MOLECULE TYPE: protein     (xi) SEQUENCE DESCRIPTION: SEQ ID NO:6:

```
Met Ala Lys Leu Ile Leu Leu Leu Thr Thr Leu Ala Leu Phe Val Leu
 1               5                  10                  15

Leu Ala Asn Ala Ser Ile Tyr Arg Thr Thr Val Glu Leu Asp Glu Glu
                20                  25                  30

Asp Asn Asp Asp Glu Asn Gln Pro Leu Cys Arg Arg Gln Phe Gln Gln
            35                  40                  45

His Gln Gln Val Arg Ala Cys Gln Arg Tyr Leu Arg Arg Arg Ala Gln
     50                  55                  60

Arg Gly Gly Leu Ala Asp Glu Leu Glu Leu Glu Asp Val Glu Glu Asn
 65                  70                  75                  80

Glu Asp Glu Asp Glu Asn Gln Gln Arg Gly Pro Ala Leu Arg Leu Cys
                 85                  90                  95

Cys Asn Gln Leu Arg Gln Val Asn Lys Pro Cys Val Cys Pro Val Leu
                100                 105                 110

Arg Gln Ala Ala His Gln Gln Leu Tyr Gln Gly Gln Ile Glu Gly Pro
               115                 120                 125

Arg Gln Val Arg Arg Leu Phe Arg Ala Ala Arg Asn Leu Pro Asn Ile
           130                 135                 140

Cys Lys Ile Pro Ala Val Gly Arg Cys Gln Phe Thr Arg Trp
145                 150                 155
```

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear     (xi) SEQUENCE DESCRIPTION: SEQ ID NO:7:

GGCGGACAGC CCTATGAGCT TGAAGAC                                        27

(2) INFORMATION FOR SEQ ID NO:8:

(i) SEQUENCE CHARACTERISTICS:
        (A) LENGTH: 27 base pairs
        (B) TYPE: nucleic acid

```
            (C) STRANDEDNESS: single
            (D) TOPOLOGY: linear (xi) SEQUENCE DESCRIPTION: SEQ ID NO:8:

GGCGGACAGC CCGCTGAGCT TGAAGAC                                              27

(2) INFORMATION FOR SEQ ID NO:9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:9:

AACGATGACG AAACCCAGCC AAGGCGA                                              27

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:10:

AACGATGACG AAATCCAGCC AAGGCGA                                              27
```